(12) United States Patent
Chan et al.

(10) Patent No.: US 8,435,234 B2
(45) Date of Patent: May 7, 2013

(54) METHOD AND APPARATUS FOR MONITORING AND CONTROLLING LASER-INDUCED TISSUE TREATMENT

(75) Inventors: Kin F. Chan, San Jose, CA (US); Leonard C. DeBenedictis, Palo Alto, CA (US)

(73) Assignee: Reliant Technologies, Inc., Hayward, CA (US)

(*) Notice: Subject to any disclaimer, the term of this patent is extended or adjusted under 35 U.S.C. 154(b) by 780 days.

(21) Appl. No.: 11/983,334

(22) Filed: Nov. 7, 2007

(65) Prior Publication Data

US 2008/0188839 A1 Aug. 7, 2008

Related U.S. Application Data

(60) Provisional application No. 60/888,482, filed on Feb. 6, 2007.

(51) Int. Cl.
*A61B 18/18* (2006.01)

(52) U.S. Cl.
USPC ....... 606/9; 606/10; 606/13; 607/88; 128/898

(58) Field of Classification Search .................. None
See application file for complete search history.

(56) References Cited

U.S. PATENT DOCUMENTS

| | | | |
|---|---|---|---|
| 5,735,844 A * | 4/1998 | Anderson et al. | 606/9 |
| 5,906,609 A | 5/1999 | Assa et al. | |
| 6,171,302 B1 | 1/2001 | Talpalriu et al. | |
| 6,273,884 B1 | 8/2001 | Altshuler et al. | |
| 6,406,474 B1 | 6/2002 | Neuberger et al. | |
| 6,695,835 B2 | 2/2004 | Furuno et al. | |
| 6,758,845 B1 | 7/2004 | Weckwerth et al. | |
| 7,135,033 B2 | 11/2006 | Altshuler et al. | |
| 7,204,832 B2 | 4/2007 | Altshuler et al. | |
| 2003/0032950 A1 | 2/2003 | Altshuler et al. | |
| 2003/0034959 A1 | 2/2003 | Davis et al. | |
| 2003/0167033 A1 * | 9/2003 | Chen et al. | 604/20 |

(Continued)

FOREIGN PATENT DOCUMENTS

| | | |
|---|---|---|
| WO | WO 01/23032 A2 | 4/2001 |
| WO | WO 01/26573 A1 | 4/2001 |
| WO | WO 2004/086947 A2 | 10/2004 |
| WO | WO 2005/016453 A1 | 2/2005 |

OTHER PUBLICATIONS

PCT International Search Report and Written Opinion, PCT/US07/023621, May 21, 2008, 9 pages.

(Continued)

*Primary Examiner* — Bill Thomson
*Assistant Examiner* — Lynsey Crandall
(74) *Attorney, Agent, or Firm* — Wood, Herron & Evans, LLP

(57) ABSTRACT

The present invention relates to a method and apparatus for using an imaging detector to image an optical pattern created by illumination of a viscous material that is applied to the skin. The viscous material forms a detectable pattern that can be imaged by the imaging detector. In some examples, the viscous material is reflective and allows reflection from an illumination source to create an optical pattern on the imaging detector. In other cases, the variation in thickness of an absorbing or scattering viscous substance can be imaged by the detector. Polarized illumination and detection can be used to enhance the response.

26 Claims, 5 Drawing Sheets

U.S. PATENT DOCUMENTS

| | | |
|---|---|---|
| 2003/0216719 A1 | 11/2003 | DeBenedictis et al. |
| 2003/0220632 A1* | 11/2003 | Strasser et al. .................... 606/9 |
| 2004/0100444 A1 | 5/2004 | Park et al. |
| 2004/0133251 A1* | 7/2004 | Altshuler et al. ............... 607/88 |
| 2005/0062720 A1 | 3/2005 | Rotzoll et al. |
| 2005/0107852 A1 | 5/2005 | Levernier et al. |
| 2005/0141068 A1 | 6/2005 | DeBenedictis et al. |
| 2005/0143719 A1 | 6/2005 | Sink |
| 2005/0148907 A1* | 7/2005 | Skover et al. .................... 601/17 |
| 2005/0154380 A1* | 7/2005 | DeBenedictis et al. ........... 606/9 |
| 2005/0278002 A1* | 12/2005 | Eimerl et al. .................... 607/88 |
| 2005/0285928 A1 | 12/2005 | Broome et al. |
| 2006/0011024 A1 | 1/2006 | Azar et al. |
| 2007/0093797 A1 | 4/2007 | Chan et al. |

OTHER PUBLICATIONS

Fujii, H. et al., "Multispot Laser Photocoagulation System Using a Fiber Bundle Scanner", Applied Optics, Oct. 1, 1982, pp. 3437-3442, vol. 21, No. 19.

Manstein, D. et al., "Fractional Photothermolysis: A New Concept for Cutaneous Remodeling Using Microscopic Patterns of Thermal Injury," Lasers in Surgery and Medicine, 2004, pp. 426-438, vol. 34.

U.S. Appl. No. 60/458,770, filed Mar. 27, 2003, 36 pages.

U.S. Appl. No. 10/745,761, filed Dec. 23, 2003, 33 pages.

U.S. Appl. No. 11/737,696, filed Apr. 19, 2007, 63 pages.

* cited by examiner

METHOD AND APPARATUS FOR MONITORING AND CONTROLLING LASER-INDUCED TISSUE TREATMENT

CROSS-REFERENCE TO RELATED APPLICATION

This application claims priority under 35 U.S.C. §119(e) to U.S. Provisional Patent Application Ser. No. 60/888,482, "Method And Apparatus For Monitoring And Controlling Laser-Induced Tissue Treatment," filed Feb. 6, 2007 by Kin F. Chan and Leonard C. DeBenedictis. The subject matter of all of the foregoing is incorporated herein by reference in its entirety.

BACKGROUND OF THE INVENTION

1. Field of the Invention

The present invention relates to a method and apparatus for dermatological tissue treatment, and more particularly, to a method and apparatus comprising a combination of a light source, a handpiece, and an optical means for measurement of the handpiece motion utilized for controlling the tissue treatment.

2. Description of the Related Art

Lasers and other intense light sources are used for various types of tissue treatment, including dermatological tissue treatment. During dermatological tissue treatment utilizing light, a light beam irradiates the skin surface of a patient. Generally, lasers that are used for such treatment operate at a wavelength that is absorbed by one of the natural chromophores in the skin, such as water. In the case of water as the primary chromophore, cellular and interstitial water absorbs light energy and transforms the light energy into thermal energy. The transport of thermal energy in tissues during treatment is a complex process involving conduction, convection, radiation, metabolism, evaporation and phase change that vary with the operational parameters of the light beam. It is important in such procedures not to damage tissue underlying or surrounding the target tissue area. If the light beam optical operational parameters, such as wavelength, power, the intensity of the light, pulse duration, rate of emission, etc. are properly selected, cellular and interstitial water in the patient's skin is heated causing temperature increases that produce a desired dermatological effect. Conversely, improper selection of the optical operational parameters can result in undertreatment or overtreatment of the tissue. Therefore, it is desirable to accurately control optical operational parameters used in the treatment so that the light is delivered to the tissue in a controlled manner. A variety of devices have been proposed that intelligently control laser beam power, intensity, duration, etc. However, as will be discussed in greater detail below, application of these devices have significant disadvantages.

Known devices for dermatological tissue treatment include a hand-held delivery apparatus, sometimes referred to as a handpiece. A handpiece is the preferred means by which physicians apply treatment to tissue. During treatment, the handpiece emitting light is moved by a physician's hand along the tissue to be treated. Treatment level from such a device is typically set in advance by manually selecting the light beam operational parameters. The operational parameters, which for example include power level, energy, pulsation rate, temperature, light intensity, and current, determine the degree of treatment of the entire treatment process.

One disadvantage of some of the existing handpiece apparatuses is that they require strict precision in positioning of the handpiece and application of controlled movement in order to stay within limits of safe, uniform and efficacious treatment. Theoretically, strict precision can be achieved with a high degree of skill, attention and dexterity from the treating physician. In a real procedure, however, manual application and control of the handpiece can easily result in non-uniformity of treatment due to imprecise or involuntary movements of the human hand and/or uneven tissue surfaces. This often results in either some areas of the targeted tissue being under-treated, or causes some areas to be over-treated.

A typical approach of known handpieces is to produce a macroscopic, pulsed treatment beam that is manually moved from one area of the skin to another in a patchwork like manner in order to treat a larger region of skin tissue. Such an approach has the disadvantage of producing artifacts and sharp boundaries associated with the inaccurate positioning of the individual treatments with respect to the treated skin surface.

Another disadvantage of known handpieces is that, as discussed above, the laser operational parameters defining the selected level of treatment are typically pre-set once for the entire course of treatment. The individual tissue properties of each patient are factored-in based on a preliminary tissue assessment prior to the treatment and the treatment can proceed using the predetermined operational parameters.

For example, some existing handpiece apparatuses provide feedback indicating to the physician the rate of the handpiece movement which allows the physician to adjust the treatment speed. But this handpiece apparatus requires the physician to treat at a pre-selected rate of motion. The disadvantage of this apparatus is that it restricts the physician to a single treatment speed. In large flat areas, such as the cheek, it is desirable to treat at a high speed. In highly contoured areas, such as the lip, it is desirable to treat at a lower speed. Restricting the physician to a pre-selected rate of motion limits the flexibility of the physician when treating regions, such as the face, that include both large flat areas and highly contoured areas that are in close proximity. Additionally, if the speed of the handpiece changes during the treatment procedure, the apparatus does not provide for automatic adjustment of its operational parameters to compensate for the changed rate of movement, leading to uneven treatment.

The application of robotic means used in the field of dermatological or cosmetic surgery could overcome the limitation of human imprecision. However, one disadvantage of typical conventional robotic apparatuses is that they lack the necessary direction and judgment in treatment that a physician provides. Although robotics is precise, it is not typically intelligent enough to make complex choices or react to unforeseen circumstances during treatment. Additionally, robots deprive a physician of discretion in an aesthetic sense.

Another disadvantage of the typical conventional robotic apparatus is that the full treatment may require complete immobilization of the patient. Alternatively, a sophisticated image stabilization system must be employed to compensate for patient's movement. It is still another disadvantage of such robotic apparatuses that they are bulky and cannot be easily moved into treatment positions in relation to the areas allowing little room for movement. Rather, a tissue surface to be treated has to be brought into a specific position in relation to the apparatus before treatment can take place.

A disadvantage of the use of known handpieces that depend on optical resolution of features on the skin is that in areas where there are few features, indistinct features, or no features on the skin, inconsistent results can be obtained. This is particularly true when a window in the optical field of a motion sensor element is placed in contact with the skin or in contact with an ointment applied to the skin. The application of a dye such as FD&C Blue No. 1 can solve these problems, but the application of such visible dyes can be an inconvenient extra step in a treatment process and the visible dyes can be time consuming to remove.

Thus, there is a need for method and apparatus which reduce some or all of the problems associated with the existing laser-induced handpieces apparatuses and robotics.

SUMMARY OF THE INVENTION

The present invention overcomes the limitations of the prior art through the use of a detector in a handpiece to detect patterns of illumination that are formed by a viscous material that is applied to the skin.

In some embodiments of the invention, the method comprises applying a viscous material to a region of skin tissue to be treated; emitting treatment energy from a handpiece towards the region, the treatment energy having at least one operational parameter affecting a dosage of the tissue treatment; moving the handpiece, wherein the movement of the handpiece is defined by at least one variable positional parameter and that variation in at least one positional parameter affects the dosage of the tissue treatment; directing illumination toward the viscous material; measuring in real-time using a detector a variation in at least one positional parameter, wherein the measuring comprises detecting a pattern of the illumination that is reflected from the viscous material; and controllably adjusting in real-time at least one of the operational parameters in response to the variation in at least one positional parameter.

In some embodiments, the measuring may further comprise imaging an optical pattern formed by the viscous material.

Some embodiments of the invention comprise measuring a variation in at least one positional parameter, wherein the measuring includes detecting the illumination wherein the detection is enhanced by the presence of the viscous material.

The detector may comprise an optical mouse. The treatment may be a fractional or bulk treatment. The operational parameter may include, for example, treatment zone density, pulse duration, pulse timing, treatment zone size, and treatment power.

In some embodiments of the invention, the viscous material is thixotropic and/or shear thinning.

In some embodiments of the invention, the handpiece can be configured to form patterns in a viscous material applied to the skin surface. In some embodiments, the handpiece tip comprises rollers or elongated runners.

In some embodiments of the invention, the dermatological treatment can be a cosmetic treatment, for example a cosmetic treatment of wrinkles.

In some embodiments of the invention, the method comprises directing illumination toward the tissue to be treated; emitting treatment energy from a handpiece towards a skin tissue to be treated, the treatment energy having at least one operational parameter affecting a dosage of the pre-selected tissue treatment; moving the handpiece, wherein the movement of the handpiece is defined by at least one variable positional parameter and that variation in at least one positional parameter affects the dosage of the tissue treatment; detecting the illumination using a polarization sensitive sensor; measuring in real-time using the polarization sensitive sensor a variation in at least one positional parameter; and controllably adjusting in real-time at least one of the operational parameters in response to the variation in at least one positional parameter.

In some embodiments, the polarization of the detection can be parallel or cross to the polarization of the illumination.

Other aspects of the invention include apparatuses corresponding to the methods described above.

BRIEF DESCRIPTION OF THE DRAWINGS

The invention has other advantages and features which will be more readily apparent from the following detailed description of the invention and the appended claims, when taken in conjunction with the accompanying drawings, in which:

DETAILED DESCRIPTION OF THE PREFERRED EMBODIMENTS

The usefulness of the measurement positional parameters of a handpiece has been described in copending U.S. patent application Ser. No. 11/020,648 by DeBenedictis et al. (entitled "Method and apparatus for monitoring and controlling laser-induced tissue treatment", filed Dec. 21, 2004), which is herein incorporated by reference. Examples of positional parameters include velocity, speed, position, change in position, and acceleration of the handpiece relative to the treatment region. The DeBenedictis '648 patent application describes a method for detecting positional parameters using an imaging detector such as an optical mouse chip in conjunction with a contrast enhancing agent that is applied to the skin.

The present invention relates to a method and apparatus for using an imaging detector to image an optical pattern created by illumination of a viscous material that is applied to the skin. The viscous material forms a detectable pattern that can be imaged by the imaging detector. In some examples, the viscous material is reflective and allows reflection from an illumination source to create an optical pattern on the imaging detector. In other cases, the variation in thickness of an absorbing or scattering viscous substance can be imaged by the detector. Polarized illumination and detection can be used to enhance the response. Reflections of the illumination are beneficial because, in combination with automatic gain control circuitry, they can provide images with sharp boundaries relative to those created using scattering from a uniform medium.

Figure 1:
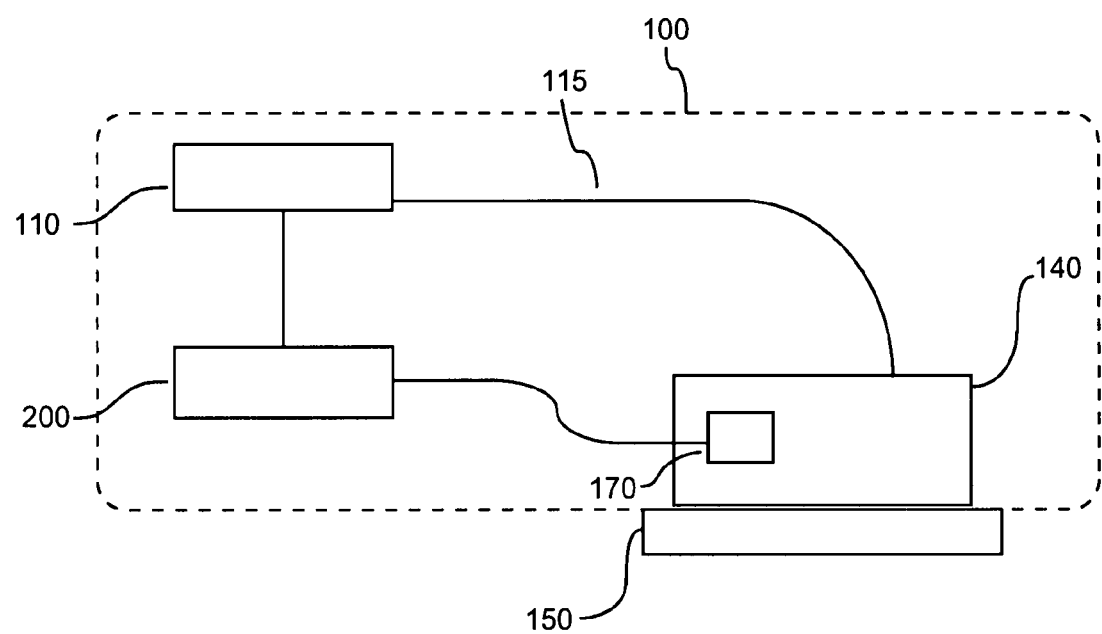
FIG. 1 is a diagrammatic view of an apparatus according to the invention showing feedback control of the laser power for controlled tissue treatment.

In accordance with the exemplary embodiment shown in FIG. 1, apparatus 100 comprises treatment energy source 110; treatment energy guide 115 for transmission of the treatment energy to the handpiece 140; movable handpiece 140 is coupled to the treatment energy guide 115 for directing of the treatment energy towards target area of the skin 150; imaging detector 170 for detecting variations in positional parameters of handpiece 140; and controller 200 for controlling operational parameters of the treatment energy or its delivery in response to the detected variations in the handpiece positional parameters.

The treatment energy source 110 can include a radio-frequency source, a laser, and/or multiple light power sources arranged in an array, such as a one-dimensional array or two-dimensional array. The treatment energy delivered by the handpiece may be characterized by a particular set of operational parameters that are selected to produce a desired dermatological effect on a target area of the skin 150. Operational parameters of the treatment energy (i.e. operational parameters) can, for example, include optical fluence, power, pulsation rate, duty cycle, light intensity, timing of pulse initiation, pulse duration, radio frequency, and/or wavelength.

The treatment energy guide 115 can be any apparatus suitable for transmission of the treatment energy emitted from treatment energy source 110. For example, if the treatment energy source 110 is an optical source, then an optical fiber, optical waveguide, and/or articulating arm may be used. If the treatment energy is radio frequency, then the treatment energy guide 115 may be a waveguide and/or wires.

Figure 2:
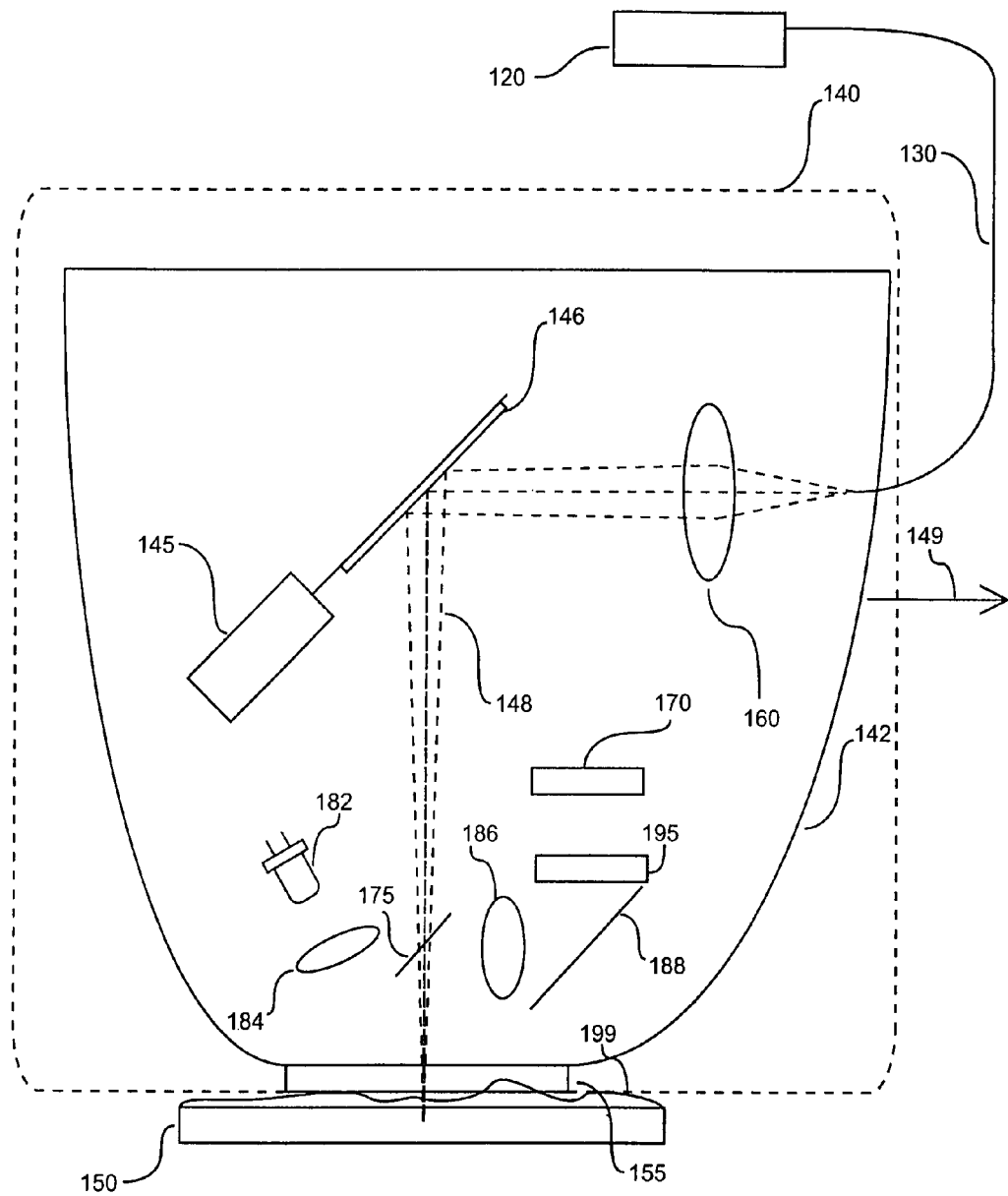
FIG. 2 illustrates an embodiment of the handpiece of the apparatus shown in FIG. 1.

FIG. 2 shows the handpiece 140 of FIG. 1 in more detail for an embodiment that illustrates the delivery of optical treatment energy to the skin 150. The handpiece 140 comprises a housing 142, which is a shell that is adapted for convenient holding by a human hand during the delivery of dermatological treatment. A light guide 130 connects a light source 120 to the handpiece 140. The light guide 130 can be, for example, an optical fiber or an articulating arm. The handpiece 140 includes an optical scanning mirror 146 connected to a galvanometer scanner 145. Other types of scanners can be used in this application in place of the galvanometer scanner 145 and the scanning mirror 146. For example, a starburst scanner could be used as described in the copending U.S. patent application Ser. No. 11/158,907, which is herein incorporated by reference. The handpiece 140 may further include one or more optical delivery lenses 160 that are optically coupled to light guide 130. Delivery lens or lenses 160 typically focus the optical beam from the optical fiber 130 on or within the skin 150. The delivery lens 160 may be implemented using one or more optical elements, including for example mirrors, optical lenses, and/or optical windows and may focus the optical beam to one or more locations. The treatment beam can be directed to pass through a dichroic beamsplitter prior to reaching the skin. The scanner mirror 146 can scan the beam across a 1-, 2-, or 3-dimensional region to be treated. The width of the area of skin 150 to be treated in each pass can be pre-selected, for example, to be about 0.5 cm to 3.0 cm. A substantial portion of the treatment beam typically passes through the viscous substance.

Optical elements 160 may be configured to allow for control of a microscopic treatment pattern and/or density of treatment zones. Substantially uniform pre-selected pattern and density of the treatment zones across the entire treated tissue area may be achieved by controlling the scanner assembly (comprising elements 145 and 146), the optical source 120, and/or optical elements 160. Typical treatment patterns include: discrete treatment zone spot diameters (i.e. at the full width half maximum (FWHM) location of the beam at the surface of the tissue) of less than about 500 µm, and preferably less than about 250 µm, and more preferably less than about 100 µm; treatment densities of between about 100 and 5000 treatment zones per square centimeter per handpiece pass over a given tissue area; separations between discrete treatment zones of greater than about 75 microns, with untreated and/or undamaged tissue between discrete treatment zones; and substantially cylindrical (or ellipsoid) treatment zones with the axis of the cylinder (or the major axis of the ellipsoid) typically perpendicular to the surface of the tissue. Embodiments of the present invention may produce other treatment patterns and dimensions as disclosed, for example, in co-pending U.S. patent application Ser. No. 10/888,356 entitled "Method and Apparatus for Fractional Photo Therapy of Skin", filed on Jul. 9, 2004, and incorporated herein by reference.

Handpiece 140 can be positioned relative to the target area of skin 150 using a mechanical separation, which may be incorporated into the handpiece shell 142 as shown in FIG. 2 to achieve a particular beam shape or size at the target tissue or to focus the beam at a particular depth within the tissue. The handpiece can be moved at a substantially constant or variable velocity, such as along direction 149, of approximately between about 0.5 cm/s and about 10 cm/s, and more preferably between about 2 cm/s and about 6 cm/s, depending on the location of the treatment area. When the positional parameters vary, the dosage, density, and pattern of the delivered treatment can be preserved at the pre-selected level. Preservation of the pre-selected treatment parameters is accomplished by adjustment of the operational parameters of apparatus 100 by the controller 200. A change in the treatment level due to a change in positional parameters may be substantially compensated by adjusting the optical power or pulse timing of the treatment energy source 110 (e.g. the light source 120 of FIG. 2).

Compensation for positional parameters can be accomplished in several ways. Some of these ways are described in more detail in the copending DeBenedictis '648 patent application. In particular embodiments, such as a pulsed fractional laser treatment system, treatment dosage can be proportional to (1) the number of pulses per linear mm of treatment, (2) the laser power, and (3) the laser pulse duration. To maintain a desired constant treatment dosage as handpiece velocity is changed, any of these three parameters can be changed. Other parameters that affect dosage will be evident to those skilled in the art. For handpiece speeds lower than a selected minimum, such as 5 mm/s, the treatment can be turned off as a safety feature that prevents noise in the detection circuit from causing a large percentage change in the treatment dosage.

Figure 3:
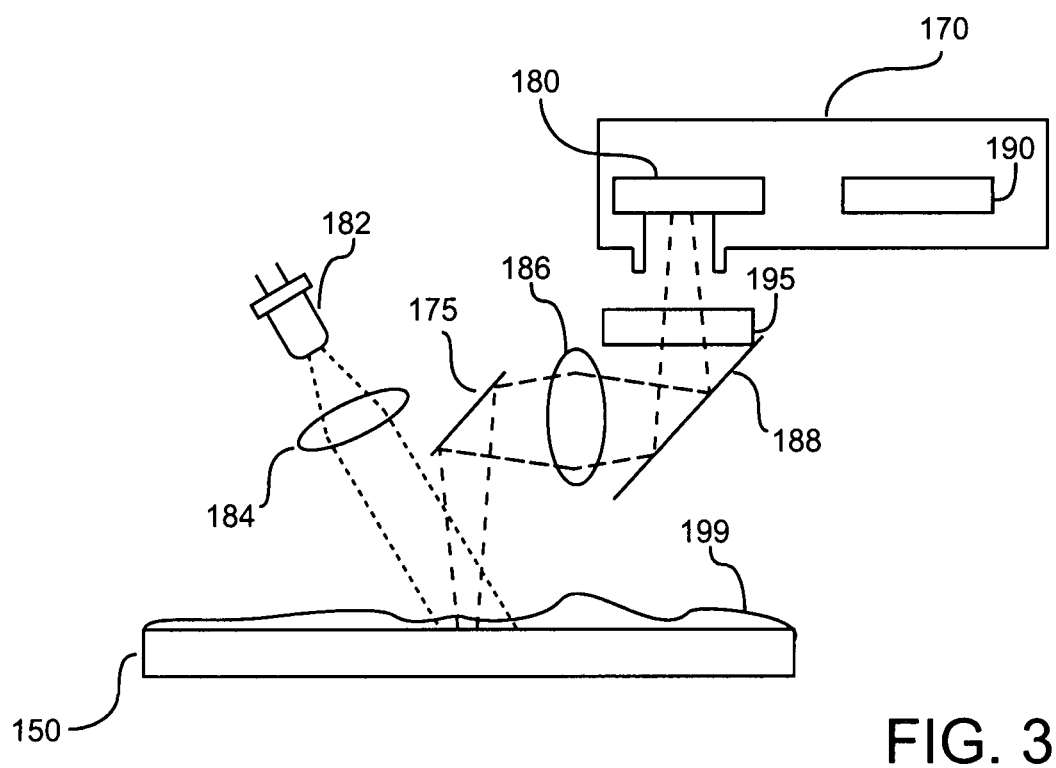
FIG. 3 illustrates the sensing operation of the handpiece shown in FIG. 2.

Handpiece 140 of FIG. 2 advantageously includes detector 170 for detecting variations in the positional parameters of handpiece 140. The basic operating principle of the optical navigation technique is shown in FIG. 3. Detector 170 may be an optical navigation device that allows quantitative measurement of the movement of handpiece 140. Illumination source 182 illuminates the surface of the tissue underneath handpiece 140. The illumination source 182 can be, for example, an LED or a laser diode. The illumination is collimated or focused by means of lens 184 on the treated surface to be reflected from features of the viscous substance 199 that is applied to the skin 150. Illumination that is reflected and/or scattered from the viscous substance is captured by imaging lens 186 to form an image on sensor 180 following reflection from a dichroic mirror 175. A dichroic mirror 175 is used so that the treatment beam can be overlapped with the region of the viscous substance 199 that is imaged by the sensor 180. An optional imaging mirror 188 can be used to direct the image upwards if desired for mechanical reasons. Sensor 180 continuously takes pictures of the points in the treated area at high speed as handpiece 140 moves. The image capture rate of sensor 180 is sufficiently high to allow sequential pictures to overlap. Sequential images from the sensor 180 are sent to image processing device 190.

The handpiece 140 may further comprise a polarizer 195. The polarizer 195 can be oriented at the optical path of the sensor 180 to enhance or suppress certain types of reflection (e.g. glare) of the incident illumination. In some embodiments, the illumination is polarized and the polarizer 195 can be oriented such to pass reflections that are parallel to the incident illumination. The combination of a polarizer and a sensor 180 form a polarization sensitive sensor. This will enhance the spectrally reflected portion of the incident illumination. In cases where the skin itself has sufficient features for the sensor to detect, the polarizer 195 can be oriented cross to the incident illumination to reduce the portion of the illumination that is reflected from the viscous material 199.

Detector 170 can comprise an imaging sensor 180 for repeatedly capturing images of a viscous substance 199 that is applied to target area 150 and an image processing device 190 for analyzing in real-time varying positional parameters of the moving handpiece 140. The captured images can comprise patterns of specularly reflected illumination from the illumination source 182 that is incident on the viscous substance 199.

Image processing device 190 may comprise a programmable digital computer that uses optical navigation engine for analyzing the sequential images captured by sensor 180. Image processing device 190 can be designed to use an image-processing algorithm of optical navigation engine to identify the common features between the images. Difference between two sequential images corresponds to changes in the position, velocity and distance of handpiece 140 relative to the skin 150 at two sequential points in time. Preferably, controller 200 stores a set of rules for determining conditions suitable for dermatological treatment based on the set of one or more positional parameters measured by detector 170. The set of rules may be stored in a file associated with a particular type of treatment or in a file associated with the treatment designed for a particular patient, so that different patients can have different treatment conditions. The rules may include a rule expressed as a variable operational parameter calculated based on one or more variations in measurements of positional parameters. The rules may also include an upper and lower bound for the positional parameters, and a resulting outcome in case the variable operational parameter exceeds or falls below the acceptable threshold.

Possible outcomes from controller 200 can include triggering an "operation" mode and a "stop" mode. In the "operation" mode, the treatment continues, as will be discussed in greater detail below, and the operational parameters of the apparatus 100 are monitored in real-time in response to the signals indicative of the changes in the handpiece positional parameters. In the "stop" mode, controller 200 immediately halts all operations of apparatus 100 in response to detecting a significant change in treatment conditions that render the continuation of treatment unsafe or ineffective. Specifically, treatment with the dosage level that exceeds the lower threshold, but is below the upper threshold is considered acceptable. Treatment at a dosage level that exceeds the upper threshold or is below the lower threshold level may require shutdown of apparatus 100.

A specific example of a detector 170 that can be used in apparatus 100 is an optical mouse package produced by Avago Technologies, Inc. of San Jose, Calif., and particularly the ADNS 2600 and the ADNS 3080 series optical mouse packages. One beneficial feature of the Avago Technologies optical mice is that they incorporate automatic gain control that can be particularly useful with specular reflections since the intensity of these reflections can cover a wide dynamic range in the resultant image on the sensor 180. The optical mouse package includes both a sensor 180 and an image processing device 190. If such an optical navigation sensor is used for detector 170, then in some cases the imaging can be inconsistent, particularly on very light skin (e.g. type I skin) with few dermatological features that the sensor 180 can detect. The DeBenedictis '648 application described the application of a contrast enhancing agent to overcome this problem.

Figure 4A:
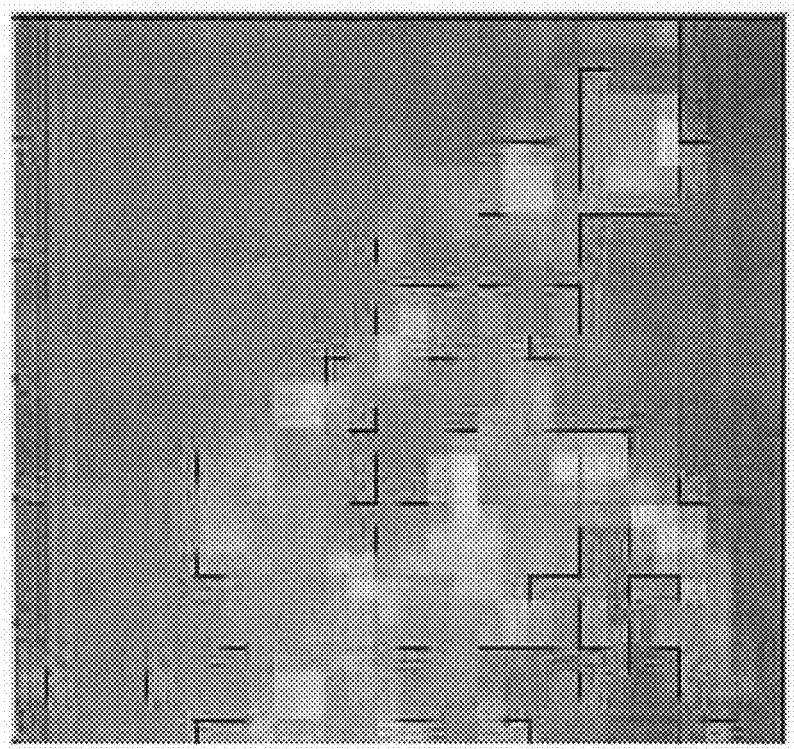
FIG. 4 shows two images of specular reflections from a viscous material as captured by a detector.
Figure 4B:
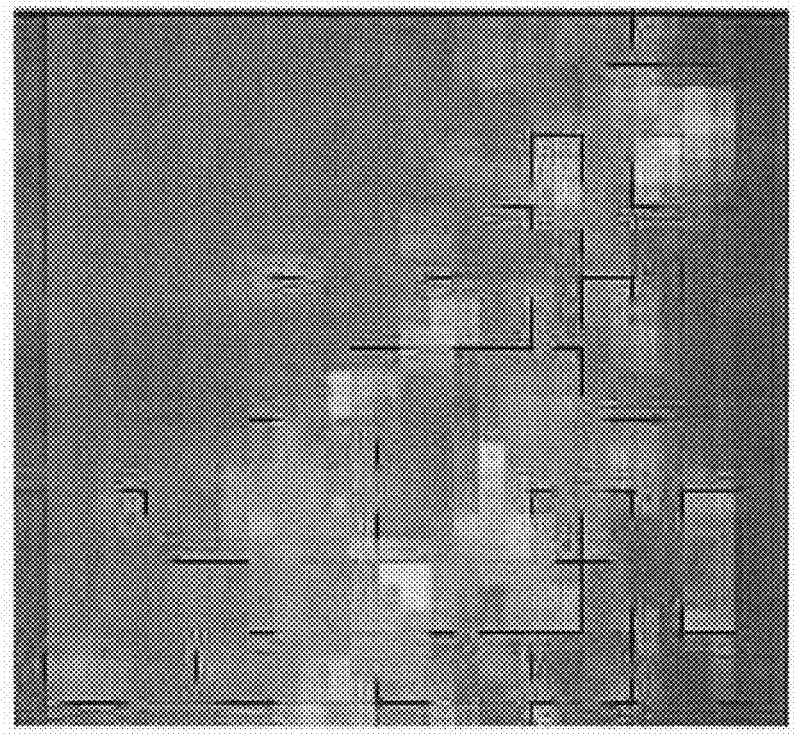

It has been discovered that the patterns created by the imaging system can be particularly enhanced by applying a viscous substance 199 to the skin 150 to create a pattern that can be imaged using the imaging system depicted in FIG. 3. A more distinct pattern can be created in a specific manner by applying a viscous material 199 to the skin surface. The high viscosity material creates a pattern of ridges that retain their shape as the detector 170 measures changes in one or more positional parameters of the handpiece 140. Since the imaging system can primarily image the features of the viscous material 199, the detection of positional parameters by the detector 170 can be made to be nearly independent of skin type and texture by applying a viscous material 199 to the skin 150. Examples of sequential images captured from a viscous substance 199 are shown in FIGS. 4A and 4B.

The preferred choice of viscous material depends on the optical system and the tip configuration. For example, for many applications it is important to create a balance between allowing the viscous material 199 to have a low enough viscosity to be spread easily onto the skin and to allow it to conform under the movement of the tip over the substance, while also being viscous enough to hold a sufficiently rigid shape in the portions being sensed by the detector 170 to measure positional parameters.

Figure 5:
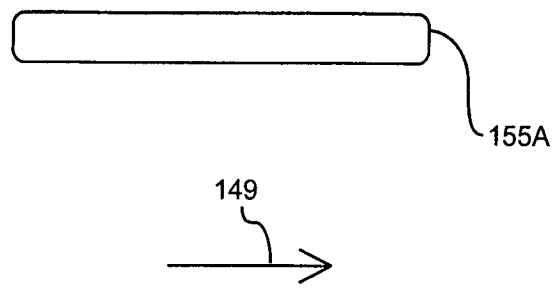
FIG. 5 illustrates a top view of an elongated runner configuration for the tip of the handpiece.
Figure 5:
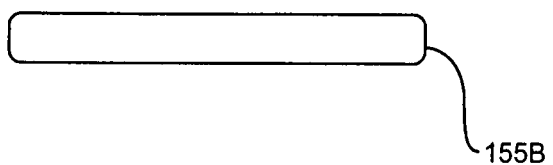
Figure 6:
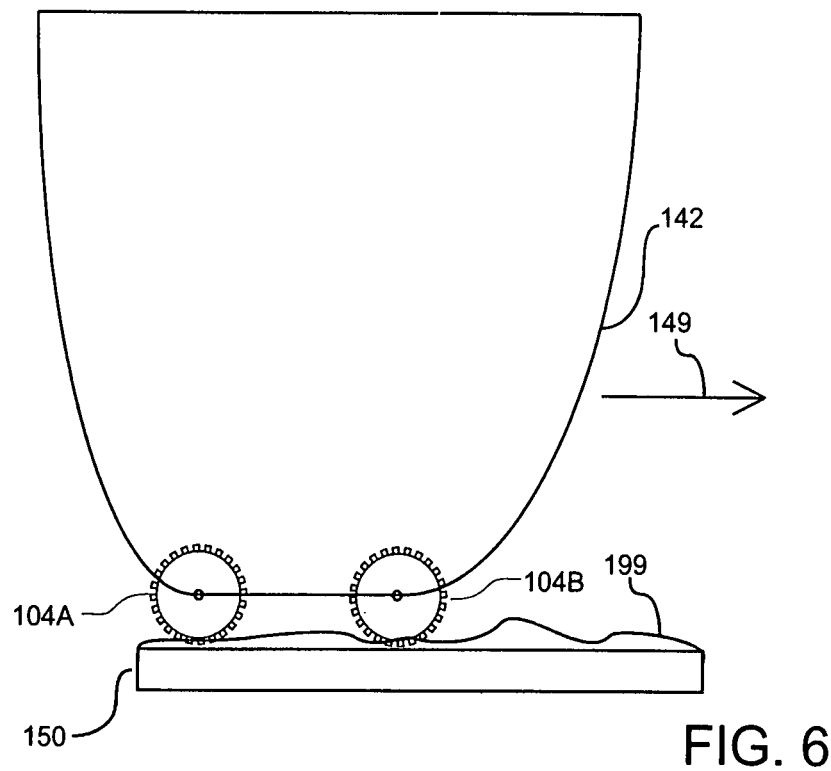
FIG. 6 illustrates a side view of a roller configuration for the tip of the handpiece.

Two examples of handpiece tip configuration are shown in FIGS. 5 and 6. In one embodiment, the handpiece slides across the skin primarily on two elongated runners 155A,B as depicted in profile in FIG. 2 and top view in FIG. 5. An alternate embodiment is shown in FIG. 6 wherein the end of the handpiece comprises one or more rollers 104A,B that roll along the direction 149 of handpiece motion relative to skin 150. Other embodiments can be employed depending on desired characteristics, for example textured rollerballs similar to those used in mechanical mice for desktop computers could be used to allow easier motion in two dimensions. Each specific configuration will have its own limitations and benefits. For example, the roller configuration may provide reduced drag on the handpiece relative to the elongated runners and the spinning rollers can provide visual feedback to indicate the handpiece is in contact with the skin 150 and/or the viscous material 199 across the length of the treatment area. The elongated runner configuration has the advantage that the viscous material 199 can be of higher viscosity than may be permitted with the rollers because the rollers may trap some of the viscous material 199 if too much pressure is applied to the handpiece for certain choices for viscous material 199, which could impede proper imaging. Other mechanical solutions to this problem will be evident to those skilled in the art. A combination of the elongated runner and the roller configuration may also be used. Both the elongated runner and the roller configurations allow deformation of the skin, but the deformation is limited in each case by the elongated runners or the rollers respectively. The skin deformation could be reduced by employing both the elongated runners and the rollers to limit the skin deformation in the two dimensions of the skin surface rather than just one.

A viscous material 199 is a material with a high coefficient of viscosity, which is defined as the ratio of the tangential frictional force per unit area to the velocity gradient perpendicular to the direction of flow. Low viscosity materials have been tested and these typically do not enhance the response of the sensor 180 as well and can even provide worse tracking than with the absence of the substance. It is believed that these non-viscous materials flow to fill in the surface of the skin and reduce the features that are present on the skin, such as small dermatoglyphs, thus reducing the reliability of tracking. Thus, it is believed that low viscosity fluids do not present enough texture for the imaging system to reliably track spectral reflections in many cases. Testing has shown that substances with effective viscosities less than about $10^3$ centipoise (cP) are usually not good candidates for the process described by this invention. For clarity, examples of viscous materials 199 are VASELINE petroleum jelly (Unilever Nev., Rotterdam, Netherlands), which has a viscosity of about $6.4*10^4$ cP; AQUAPHOR ointment (Beiersdorf Aktiengesellschaft, Hamburg, Germany), which comprises a mixture of petroleum jelly, mineral oil, ceresin, and lanolin alcohol; ALBOLENE moisturizing cleanser (DSE Healthcare Solutions, Edison, N.J.), which is a mixture comprising mineral oil, petrolatum paraffin, ceresin, and beta-carotene; and LIPOTHENE 133 gel (Lipothene, Inc., Pacific Grove, Calif.), which is a lipophilic, oleaginous vehicle. Examples of materials that are not viscous for purposes of this application are water (1 cP), Linseed oil (64 cP), and castor oil ($10^3$ cP). The viscosity that is the upper limit can depend on the specific embodiment, and may depend for example on the roller size, roller friction with skin surface, elongated runner material, elongated runner shape, pressure applied between handpiece and treatment surface, roller friction between roller and roller axis, adhesion between material and roller, etc. In some embodiments, the viscous material 199 has a viscosity of above $8*10^3$ cP, about $2*10^3$ cP to about $1*10^8$ cP, or $1*10^4$ cP to $1*10^5$ cP. For purposes of this application, the viscosity of a material should be measured in conditions similar to those observed during the time where the viscous material is sensed by the detector 170. A material with too high of a viscosity may affect the focal position of the beam depending on the thickness of application and thus produce variable results from treatment to treatment for precisely focused optical systems. Substances with viscosities that are above these ranges can also be used, particularly with optical systems that are less sensitive to focal spot size as the distance between the handpiece 140 and the skin 150 is varied.

Some viscous materials are shear thinning substances. These substances have a viscosity that is lower for higher shear rates over a range of desired use. Other viscous substances are thixotropic. These substances have a reduction in viscosity with time as a constant shear stress is applied. Both shear thinning and thixotropic viscous substances have the advantage of allowing them to be spread onto the skin and also to flow at least slightly as the handpiece 140 is moved across the skin 150, while also forming sufficiently rigid features to allow imaging of features in the viscous substance 199. Examples of materials that are both shear thinning and thixotropic are VASELINE petroleum jelly, AQUAPHOR ointment, ALBOLENE moisturizing cleanser, LIPOTHENE 133 gel, and many ointments. Other examples of viscous substances that are both shear thinning and thixotropic that can be used in particular applications are many gels, such as hair gel. For example, a gel comprising a mixture of water and vinyl acetate/vinylpyrrolidone copolymer (PVP/PA) or similar fixing agent can be used.

Other properties of the viscous material can be important depending on the implementation. For example, in an optical treatment system, it can be helpful to have the viscous material be transparent at the treatment wavelength so that substantially all of the treatment energy reaches the target skin. For radio frequency applications, conductivity of the viscous material can be important. Some viscous materials, such as VASELINE petroleum jelly provide visible tracks that permit the user to see which areas have just been treated, which allows the subsequent stroke to be aligned to the previous stroke. The viscous material can be chosen based on tracking fidelity, tip clogging, ergonomics of handpiece use, and ease of removal.

The thickness of application of the viscous material can be chosen to limit the clogging of the tip and to maintain the separation between the handpiece optics and the skin within a desired range. A layer thickness of about 0.1 mm or about 0.03 mm to about 0.5 mm can be used, for example. Thinner or thicker layers can also be used depending on the application and the handpiece design.

Fluids with a high viscosity index can be useful because they can provide consistent treatment regardless of the treatment environment. High viscosity index means that the viscosity has relatively little change with temperature, while a low viscosity index means that the viscosity has a relatively large change with temperature. Higher viscosity index is not required however. Viscosity index is less important than the viscosity of the material at the typical skin temperatures achieved during treatment. Vicosity indexes of about 70 to about 100 and about 50 to about 150 are particularly beneficial. Materials spanning these ranges are available and well known by those skilled in the art.

Alternatively, a low viscosity index can be used beneficially with surface cooling, for example air cooling with a ZIMMER chiller. The ZIMMER chiller or other device that cools the surface of the fluid may be used to create a gradient within the fluid such that the surface of the material is cooler than the rest of the fluid which allows it to retain its shape at the surface while the material underneath the surface is more fluid. For example, a viscosity index of about 10 to about 45 can be used.

Although the detailed description contains many specifics, these should not be construed as limiting the scope of the invention but merely as illustrating different examples and aspects of the invention. It should be appreciated that the scope of the invention includes other embodiments not discussed in detail above. Various other modifications, changes and variations which will be apparent to those skilled in the art may be made in the arrangement, operation and details of the method and apparatus of the present invention disclosed herein without departing from the spirit and scope of the invention as defined in the appended claims. Therefore, the scope of the invention should be determined by the appended claims and their legal equivalents. Furthermore, no element, component or method step is intended to be dedicated to the public regardless of whether the element, component or method step is explicitly recited in the claims.

In the claims, reference to an element in the singular is not intended to mean "one and only one" unless explicitly stated, but rather is meant to mean "one or more." In addition, it is not necessary for a device or method to address every problem that is solvable by different embodiments of the invention in order to be encompassed by the claims.

What is claimed is:

1. A method of dermatological treatment, the method comprising:
applying a viscous material to a region of skin tissue to be treated;
emitting treatment energy from a handpiece towards the region of skin tissue to effect tissue treatment, the treatment energy comprising a variable operational parameter that affects a dosage of the tissue treatment;

moving the handpiece across the region of skin tissue, the movement of the handpiece comprising a variable positional parameter that affects the dosage of the tissue treatment;

forming an imageable pattern comprising a plurality of ridges of the viscous material that are produced as the viscous material conforms under the movement of the handpiece over the viscous material and across the region of skin tissue;

directing illumination toward the ridges of the viscous material in the imageable pattern;

imaging in real-time a pattern of the illumination that is reflected from the ridges of the viscous material;

determining the variation in the positional parameter from the imaged pattern of the illumination; and controllably adjusting in real-time the operational parameter in response to the variation in the positional parameter determined from the imaged pattern of the illumination, wherein the viscous material has a viscosity greater than $2*10^3$ cP such that the shape of the ridges is retained in the viscous material while the pattern of illumination is detected in real-time.

2. The method of claim 1, wherein the viscous material is thixotropic.

3. The method of claim 1, wherein the viscous material is shear thinning.

4. The method of claim 1, wherein the viscous material has a viscosity greater than $8*10^3$ cP.

5. The method of claim 1, wherein the viscous material has a viscosity in a range of about $2*10^3$ cP to about $1*10^8$ cP.

6. The method of claim 1, wherein the viscous material has a viscosity in a range of about $1*10^4$ cP to about $1*10^5$ cP.

7. The method of claim 1, wherein the viscous material comprises petroleum jelly.

8. The method of claim 1, wherein the treatment energy is optical treatment energy and the viscous material is optically transparent to the treatment energy.

9. The method of claim 1, wherein the viscous material is chosen from a group consisting of petroleum jelly, ointment, gel, and moisturizing cleanser.

10. The method of claim 1, wherein the viscous material comprises a mixture of water and a copolymer of vinyl acetate and vinylpyrrolidone.

11. The method of claim 1, wherein a thickness of the applied viscous material is in a range of about 0.03 mm to about 0.5 mm.

12. The method of claim 1, wherein a thickness of the applied viscous material is about 0.1 mm.

13. The method of claim 1, wherein the viscous material has a viscosity index in a range of about 10 to about 45.

14. The method of claim 1, wherein the viscous material has a viscosity index in a range of about 50 to about 150.

15. The method of claim 1, wherein the viscous material has a viscosity index in a range of about 70 to about 100.

16. The method of claim 1, wherein moving the handpiece comprises:

rolling the handpiece across the region of skin tissue on two or more rollers to form the ridges in the imageable patter.

17. The method of claim 1, wherein moving the handpiece comprises:

sliding the handpiece across the region of skin tissue on two or more elongated runners to form the ridges in the imageable pattern.

18. The method of claim 1, further comprising:

cooling a surface of the viscous material.

19. The method of claim 1, wherein the dermatological treatment is a cosmetic treatment.

20. The method of claim 19, wherein the dermatological treatment is a cosmetic treatment of wrinkles.

21. The method of claim 1, wherein a detector detects in real-time the pattern of the illumination that is reflected from the ridges in the imageable pattern in the viscous material, and the detector comprises an optical mouse package.

22. The method of claim 1, wherein emitting treatment energy comprises:

delivering a fractional pattern of treatment energy.

23. The method of claim 22, wherein the operational parameter comprises at least one of treatment zone density, pulse duration, pulse timing, treatment zone size, and treatment power.

24. The method of claim 22, wherein the treatment energy is delivered with spot diameters of less than about 500 μm.

25. The method of claim 1 wherein the ridges project from a surface of the region of skin tissue.

26. The method of claim 1 wherein the ridges project toward the handpiece.

* * * * *